US010835471B2

United States Patent
Grosjacques et al.

(10) Patent No.: US 10,835,471 B2
(45) Date of Patent: Nov. 17, 2020

(54) METHOD FOR DYEING KERATIN FIBERS

(71) Applicant: Henkel AG & Co. KGaA, Duesseldorf (DE)

(72) Inventors: Camille Grosjacques, Hamburg (DE); Aileen Wagner, Hamburg (DE); Susanne Hagenow, Hamburg (DE); Hartmut Manneck, Barnitz (DE); Astrid Kleen-Fehres, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 304 days.

(21) Appl. No.: 16/061,459

(22) PCT Filed: Dec. 15, 2016

(86) PCT No.: PCT/EP2016/081193
§ 371 (c)(1),
(2) Date: Jun. 12, 2018

(87) PCT Pub. No.: WO2017/102946
PCT Pub. Date: Jun. 22, 2017

(65) Prior Publication Data
US 2020/0261345 A1  Aug. 20, 2020

(30) Foreign Application Priority Data
Dec. 18, 2015  (DE) .................. 10 2015 225 897

(51) Int. Cl.
*A61Q 5/10* (2006.01)
*A61K 8/67* (2006.01)
*A61K 8/41* (2006.01)
*A61K 8/37* (2006.01)
*A61K 8/22* (2006.01)
*A61K 8/365* (2006.01)
*A61K 8/31* (2006.01)

(52) U.S. Cl.
CPC ............ *A61K 8/676* (2013.01); *A61K 8/22* (2013.01); *A61K 8/31* (2013.01); *A61K 8/365* (2013.01); *A61K 8/37* (2013.01); *A61K 8/375* (2013.01); *A61K 8/411* (2013.01); *A61K 8/415* (2013.01); *A61Q 5/10* (2013.01); *A61K 2800/4324* (2013.01); *A61K 2800/5922* (2013.01); *A61K 2800/882* (2013.01)

(58) Field of Classification Search
CPC . A61Q 5/10; A61K 8/411; A61K 8/22; A61K 8/415; A61K 8/342; A61K 8/347; A61K 8/31; A61K 8/37; A61K 8/365; A61K 8/676; A61K 8/375; A61K 2800/88; A61K 2800/4324; A61K 2800/882
See application file for complete search history.

(56) References Cited

U.S. PATENT DOCUMENTS

2003/0154562 A1* 8/2003 Sarojini ................ A61Q 5/10
                                                      8/405
2015/0283053 A1* 10/2015 Odman Schmid ..... A61K 8/064
                                                      8/416

FOREIGN PATENT DOCUMENTS

| EP | 1655056 A1 | 5/2006 |
| WO | 0197756 A2 | 12/2001 |
| WO | 03068177 A2 | 8/2003 |
| WO | 2013126657 A2 | 8/2013 |
| WO | 2015153819 A1 | 10/2015 |

OTHER PUBLICATIONS

EPO, International Search Report and Written Opinion issued in International Application No. PCT/EP2016/081193, dated Jan. 26, 2017.

* cited by examiner

*Primary Examiner* — Eisa B Elhilo
(74) *Attorney, Agent, or Firm* — Lorenz & Kopf, LLP

(57) ABSTRACT

The subject of the present disclosure is a method for coloring of human hair, comprising the following steps in the specified sequence
A) Mixing a first component (K1) with a second component (K2) to produce a first mixture (M1),
B) Mixing the mixture (M1) with a third component (K3) to produce a second mixture (M2),
C) Application of the mixture (M2) on the hair,
D) Allowing the mixture (M2) to take effect for a period of from about 30 seconds to about 45 minutes,
E) Rinsing the mixture (M2) from the hair,
wherein
the first component (K1) is a dye preparation comprising at least one oxidation dye precursor, and
the second component (K2) is a color diluent which does not contain any oxidation dye precursors or oxidants and the third component (K3) is an oxidant preparation comprising at least one oxidant.

20 Claims, No Drawings

METHOD FOR DYEING KERATIN FIBERS

CROSS-REFERENCE TO RELATED APPLICATION

This application is a U.S. National-Stage entry under 35 U.S.C. § 371 based on International Application No. PCT/EP2016/081193, filed Dec. 15, 2016 which was published under PCT Article 21(2) and which claims priority to German Application No. 10 2015 225 897.1, filed Dec. 18, 2015, which are all hereby incorporated in their entirety by reference.

TECHNICAL FIELD

The present disclosure is in the field of cosmetics and relates to methods for oxidative dyeing of hair, wherein application mixtures which are produced in a special mixing process are used.

BACKGROUND

Changing the color of keratinous fibers, more particularly of hair, constitutes an important area of modern cosmetics. Consequently, the hair's appearance can be adapted both to current fashion trends and also to the particular preferences of each and every person. Various possibilities of changing the color of hair are known to a person skilled in the art. The color of hair can be changed temporarily by employing partially-oxidizing dyes. In this process, dyes already formed diffuse from the coloring agent into the hair fibers. Dyeing with partially-oxidizing dyes causes less hair damage. The disadvantage, however, is that the colors achieved with partially-oxidizing dyes have a low permanency and can be washed out quickly.

If the consumer wants a long-lasting color result or a tint which is lighter than the original hair color, oxidative coloring agents are normally used. To achieve permanent, intense colors with corresponding fastness properties, so-called oxidative dyes are used. Such coloring agents usually contain oxidation dye precursors, so-called developer components and coupler components, which form the dyes per se under the influence of oxidants. Oxidative coloring agents are exemplified by long-lasting color results.

Level 3 colorations are often used in the hairdressing field. Level 3 colorations are oxidative coloring agents exemplified by especially good durability and especially good gray coverage.

This good durability and good gray coverage can be achieved with a high ammonia content in the colorations, which leads to strong swelling of the hair and consequently a high diffusion rate of the oxidation dye precursors into the hair. With dark tints of Level 3 colorations, the content of oxidation dye precursors is also comparatively high.

However, this ammonia content is also associated with heavy hair damage.

In the home user field, the user who would not want to tolerate this heavy hair damage with every coloration chooses Level 2 products. Level 2 products are also oxidative coloring agents, but they have lower ammonia content or an alternative, less strongly swelling alkalizing agent is used instead of ammonia. In the home user area, Level 3 and Level 2 products are packaged separately and are sold as separate products, so that the user can choose and apply either a Level 3 or a Level 2 product.

In the hairdressing field, the hairdresser offers their customers a much wider pallet of tints. Therefore, a complete Level 3 color series comprises a pallet of a wide variety of color creams, which are mixed with the normal Level 3 oxidant preparation shortly before application. For capacity and storage reasons, the hairdresser will avoid keeping a complete pallet of tints for Level 3 products and for Level 2 products in stock.

Therefore, the present disclosure addresses a first problem of providing the hairdresser a flexible and easy-to-use method that make it possible for the hairdresser to produce a Level 2 product from a Level 3 coloring product.

Furthermore, the degree of damage in the region of the hair varies from the root to the tip. Hair in the region of the hairline has recently regrown and has not been exposed to weather influences or chemical influences. The hair in the region of the tips, by contrast, is the oldest parts of the hair and thus has the heaviest damage.

In damaged hair, the cuticula, the cuticle of the hair, is damaged to a greater or lesser degree. As a result, there is generally greater color uptake on damaged hair. Therefore, if the hairline and tips are dyed with the same coloring agent, there is always the risk of an uneven coloring result with heavily damaged hair.

The present disclosure also addresses the problem of providing the hairdresser a system with which they can simply, purposefully and reproducibly reduce the dye concentration in the hair coloring agent after assessing the degree of damage of the hair to be dyed.

Production of a Level 2 coloring product from a Level 3 product and reduction of the coloring agent concentration for use on specific portions of hair can be achieved with a "dilution" of the oxidative Level 3 product. Various possibilities to achieve this are known from the prior art.

One possibility for dilution, for example, is the mixing of a ready-to-use oxidative coloring agent with a conditioner. Since conditioner is often adjusted to a slightly acidic pH value, the pH value of the coloring agent can be reduced and the extent of the hair swelling is decreased. Due to the care substances contained in the conditioner (specific polymers, silicones, ionic surfactants, etc.), however, a color shift can occur due to the dilution with the conditioner so that the color result no longer matches the desired tint.

Another possibility for dilution is the mixing of the ready-to-use oxidative coloring agent with a shampoo. Since shampoos contain large amounts of cleaning surfactants, foam can develop too heavily during use so that complete wetting of the hair with the diluted coloring agent is no longer guaranteed. If the shampoo is no longer adequately acidic, excessive amounts of shampoo are required to dilute the coloring agent.

The same problem arises if the ready-to-use agent is diluted with clean water. Since water does not contain any acid, very large amounts of water are required to lower the pH value of the coloring agent. Finally, the difference in viscosity between the water and thickened dye cream makes rapid mixing impossible.

BRIEF SUMMARY

Methods for dying human hair are provided. In an exemplary embodiment, a method of dying human hair includes the following steps in the specified sequence. A first component (K1) is mixed with a second component (K2) to produce a first mixture (M1). The first component (K1) is a dye preparation including at least one oxidation dye precursor, and the second component (K2) is a color diluent which does not include any oxidation dye precursors or oxidants. The mixture (M1) is mixed with a third component (K3) to produce a second mixture (M2), where the third component (K3) is an oxidant preparation including at least one oxidant. The second mixture (M2) is applied to the hair, and then the second mixture (M2) is allowed to take effect for a period of from about 30 seconds to about 45 minutes. After that, the second mixture (M2) is rinsed from the hair.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

It has surprisingly emerged that the coloring agent can be diluted flexibly, quickly and in a comfortable manner without the aforementioned disadvantages when the hairdresser follows a method in which a dye cream containing oxidation dye precursors is first mixed with a special "color diluter" and a homogeneous mixture is produced from the two components. This mixture is then mixed with the oxidant preparation in a subsequent step and this second mixture is applied on the hair.

A first subject of the present disclosure is a method for coloring of human hair, including the following steps in the specified sequence
A) Mixing a first component (K1) with a second component (K2) to produce a first mixture (M1),
B) Mixing the mixture (M1) with a third component (K3) to produce a second mixture (M2),
C) Application of the mixture (M2) onto the hair,
D) Allowing the mixture (M2) to take effect for a period of from about 30 seconds to about 45 minutes, and
E) Rinsing the mixture (M2) from the hair,
wherein
   the first component (K1) is a dye preparation containing at least one oxidation dye precursor, and
   the second component (K2) is a color diluent which does not contain any oxidation dye precursors or oxidants, and
   the third component (K3) is an oxidant preparation containing at least one oxidant.

The method as contemplated herein is a method for dyeing human hair in which the three components (K1), (K2) and (K3) are mixed together successively. All three components (K1), (K2) and (K3) are cosmetic agents which contain all essential ingredients in a cosmetic carrier.

In a first step A), a first cosmetic component (K1) is mixed with a second component (K2). The first component (K1) is a dye preparation which contains at least one oxidation dye precursor in a cosmetic carrier. The first component (K1) contains at least one oxidation dye precursor of the developer type and at least one oxidation dye precursor of the coupler type.

The second component (K2) is a "color diluent", wherein the second component does not contain any oxidation dye precursors, partially-oxidizing dyes or oxidants (such as hydrogen peroxide and persulfate salts).

The term "color diluent" in the present context is understood to mean a separately packaged preparation (K2) which is mixed with the dye preparation (K1), whereby the amount of the ammonia contained in component (K1) and the oxidation dye precursors should be purposefully reduced.

In other words, component (K2) is neither a dye preparation nor an oxidant preparation.

The first component (K1) and the second component (K2) can be mixed together, for example, by employing stirring or shaking, so that the first mixture (M1) is produced. As contemplated herein, the mixture (M1) is not applied onto the hair.

It has been found to be particularly advantageous that the dilution of the dye, i.e. the production of the first mixture (M1) from the dye preparation (K1) and color diluent (K2), could be achieved without initiating the dye formation from the oxidation dye precursors with the addition of the oxidant. An equivalent and reproducible coloring result could be achieved in this manner.

For this reason, the production of this first mixture (or pre-mixture) (M1) from (K1) and (K2) in step A) is a key and essential step of the method as contemplated herein.

By contrast, if a conventional oxidative dye has been produced by mixing the components (K1) and (K3) and then diluted with the component (K2), the dye formation process and the dilution take place in parallel. In this method, which is not as contemplated herein, the intensity of the final hair coloring was therefore essentially influenced by the duration of time required for the intermixing of component (K2). Therefore, the coloring results that were achieved with this method that is not as contemplated herein were less reproducible.

When the components (K1) and (K2) are mixed together completely, i.e. producing a homogeneous mixture (M1), said mixture is in turn mixed with the third component (K3) in a subsequent step B).

The third component (K3) is an oxidant preparation containing at least one oxidant. It is particularly preferred that this oxidant is hydrogen peroxide.

The first mixture (M1) can be mixed with the third component (K3) by stirring or shaking. Then the second mixture (M2) is produced by employing this mixing process in step B). The second mixture is the ready-to-apply oxidative dye which is applied on the hair.

As contemplated herein, application of the second mixture (M2) on the hair takes place in the third step C), wherein the mixture (M2) can be applied on the entire region of the hair to be colored or only on specific parts (such as the hairline or the hair lengths/tips).

After application, the mixture (M2) is left on the hair to take effect for a period of from about 30 seconds to about 45 minutes. In the process, it is possible to leave the mixture (M2) on all regions of the hair for a specific time period. In a further embodiment, however, it is also possible to choose different exposure periods for specific regions of the hair so that the exposure period in the region of the hairline, for instance, is longer than the exposure period in the region of the damaged tips.

After the exposure period, the mixture (M2) is rinsed out of the hair in step E). The rinsing can take place with water only or with the assistance of a shampoo.

Steps A) to E) are the steps of a single coloring method, i.e. as contemplated herein, all steps are performed during a coloring process that takes place within a specific time period of a maximum of about 6 hours, preferably within a maximum of about 3 hours.

According to the method as contemplated herein, the sequence of steps is also defined and takes place in the sequence A), followed by B), followed by C), followed by D), followed by E).

Therefore, a particularly preferred embodiment is a method for coloring of human hair, including the following steps in the specified sequence A) Mixing a first component (K1) with a second component (K2) to produce a first mixture (M1),
B) Mixing the mixture (M1) with a third component (K3) to produce a second mixture (M2),
C) Application of the mixture (M2) on the hair,
D) Allowing the mixture (M2) to take effect for a period of from about 30 seconds to about 45 minutes,
E) Rinsing the mixture (M2) from the hair,
wherein
the first component (K1) is a dye preparation containing at least one oxidation dye precursor of the developer type and at least one oxidation dye precursor of the coupler type in a cosmetic carrier,
the second component (K2) is a "color diluent" which does not contain any oxidation dye precursors or oxidants and
the third component (K3) is an oxidant preparation containing hydrogen peroxide in a cosmetic carrier.

The nature of the color diluent, i.e. the second component (K2), is essential for optimal dilution of the dye preparation (K1) and for a later homogeneous and reproducible color result.

In order to ensure rapid and good miscibility of the components (K1) and (K2), the component (K2) is preferably thickened with one or multiple fatty constituents and, therefore, present in the form of an emulsion.

In a particularly preferred embodiment, the inventive method for coloring of human hair is exemplified in that the second component (K2) contains one or multiple fatty constituents in a total amount of from about 5.0 to about 70.0 wt. %, preferably from about 10.0 to about 65.0 wt. %, more preferably from about 20.0 to about 60.0 wt. % and particularly from about 40.0 to about 60.0 wt. % relative to the total weight of the second component (K2).

To the extent required by the present disclosure, "fatty constituents" are organic compounds with a water solubility at room temperature (about 22° C.) and atmospheric pressure (about 760 mmHg) of less than about 1 wt. %, preferably less than about 0.1 wt.-%. The definition of fatty constituents explicitly includes only uncharged (i.e. Non-ionic) compounds. Fatty constituents have at least one saturated or unsaturated alkyl group with at least 8 C-atoms. The molecular weight of the fatty constituents is a maximum about 5000 g/mol, preferably a maximum about 2500 g/mol and even more preferably a maximum of about 1000 g/mol. The fatty constituents are neither polyoxyalkylated nor polyglycerylated compounds.

The preferred fatty constituents in this context are the constituents from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and/or hydrocarbons. The present disclosure explicitly considers only non-ionic substances to be fatty constituents. Charged compounds such as fatty acids and their salts are not considered to be fatty constituents.

The $C_{12}$-$C_{30}$ fatty alcohols can be saturated, mono or poly unsaturated, linear or branched fatty alcohols with from about 12 to about 30 C-atoms.

Examples of preferred linear, saturated $C_{12}$-$C_{30}$ fatty alcohols are dodecan-1-ol (dodecylalcohol, laurylalcohol), tetradecan-1-ol (tetradecyl alcohol, myristyl alcohol), hexadecan-1-ol (hexadecyl alcohol, cetyl alcohol, palmityl alcohol), octadecan-1-ol (octadecyl alcohol, stearyl alcohol), arachyl alcohol (eicosan-1-ol), heneicosyl alcohol (heneicosan-1-ol) and/or behenyl alcohol (docosan-1-ol).

Preferred linear, unsaturated fatty alcohols are (9Z)-octadec-9-en-1-ol (oleyl alcohol), (9E)-octadec-9-en-1-ol (elaidyl alcohol), (9Z,12Z)-octadeca-9,12-dien-1-ol (linoleyl alcohol), (9Z,12Z,15Z)-octadeca-9,12,15-trien-1-ol (linolenoyl alcohol), gadoleyl alcohol ((9Z)-eicos-9-en-1-ol), arachidon alcohol ((5Z,8Z,11Z,14Z)-eicosa-5,8,11,14-tetraen-1-ol), erucyl alcohol ((13Z)-docos-13-en-1-ol) and/or brassidyl alcohol ((13E)-docosen-1-ol).

The preferred typical branched fatty alcohols are 2-octyl-dodecanol, 2-hexyl-dodecanol and/or 2-butyl-dodecanol.

To the extent required by the present disclosure, a $C_{12}$-$C_{30}$ fatty acid triglyceride is the triester of the trivalent alcohol glycerin with three equivalent fatty acids. Both identically structured and different fatty acids within a triglyceride molecule can be involved in the ester formation.

To the extent required by the present disclosure, fatty acids are saturated or unsaturated, unbranched or branched, unsubstituted or substituted $C_{12}$-$C_{30}$ carboxylic acids. Unsaturated fatty acids can be unsaturated or polyunsaturated. The C=C double bond(s) of an unsaturated fatty acid can have the cis- or trans configuration.

Fatty acid triglycerides are exemplified by their particular suitability, for which at least one of the ester groups, based on glycerin, is formed with a fatty acid, which is selected from dodecan acid (lauric acid), tetradecan acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-Hexadec-9-enoic acid], oleic acid [(9Z)-octadec-9-enoic acid], elaidic acid [(9E)-octadec-9-enoic acid], eruca acid [(13Z)-Docos-13-enoic acid], linoleic acid [(9Z,12Z)-octadeca-9,12-dienoic acid, linoleic acid [(9Z,12Z,15Z)-octadeca-9,12,15-trienoic acid, eleostearic acid [(9Z,11E,13E)-octadeca-9,11,3-trienoic acid], arachidonic acid [(5Z,8Z,11Z,14Z)-Icosa-5,8,11,14-trienoic acid] and/or nervonic acid [(15Z)-Tetracos-15-enic acid].

The fatty acid triglycerides can also be from natural sources. The fatty acid triglycerides occurring in soy bean oil, peanut oil, sunflower oil, macadamia nut oil, drumstick tree oil, apricot kernel oil, manila oil and/or possibly hardened castor oil, and the mixtures thereof are particularly suitable for use in the product as contemplated herein.

A $C_{12}$-$C_{30}$ fatty acid monoglyceride is the monoester of the trivalent alcohol glycerin with an equivalent fatty acid. Either the middle hydroxy group of the glycerin or the final hydroxy group of the glycerin can be esterified with the fatty acid.

The $C_{12}$-$C_{30}$ fatty acid triglycerides are exemplified by their particular suitability, for which at least one hydroxy group of the glycerin is esterified, wherein the fatty acids are selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-Hexadec-9-enoic acid], oleic acid [(9Z)-octadec-9-enoic acid], elaidic acid [(9E)-octadec-9-enoic acid], erucic acid [(13Z)-Docos-13-enoic acid], linoleic acid [(9Z,12Z)-octadeca-9,12-dienoic acid, linolenic acid [(9Z,12Z,15Z)-octadeca-9,12,15-trienoic acid, eleostearic acid [(9Z,11E,13E)-octadeca-9,11,3-trienoic acid], arachidonic acid [(5Z,8Z,11Z,14Z)-Icosa-5,8,11,14-trienoic acid] or nervonic acid [(15Z)-Tetracos-15-enoic acid].

A $C_{12}$-$C_{30}$ fatty acid diglyceride is the diester of the trivalent alcohol glycerin with two equivalent fatty acids. Either the middle and an independent hydroxy group of the glycerin with two equivalent fatty acids can be esterified with two equivalent fatty acids or both final hydroxy groups of the glycerin are each esterified with one fatty acid. The glycerin can be esterified with two identically structured or two different fatty acids.

Fatty acid diglycerides are exemplified by their particular suitability, for which at least one of the ester groups, based on glycerin, is formed with a fatty acid, which is selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z,12Z)-octadeca-9,12-dienoic acid, linolenic acid [(9Z,12Z,15Z)-octadeca-9,12,15-trienoic acid, eleostearic acid [(9Z,11E,13E)-octadeca-9,11,3-trienoic acid], arachidonic acid [(5Z,8Z,11Z,14Z)-Icosa-5,8,11,14-trienoic acid] and/or nervonic acid [(15Z)-tetracos-15-enoic acid].

Hydrocarbons are compounds consisting exclusively of the atoms carbon and hydrogen with from 8 to about 80 C-atoms. In this context, aliphatic hydrocarbons such as mineral oils, liquid paraffin oils (e.g. paraffinum liquidum or paraffinum perliquidum), isoparaffin oils, semi-solid paraffin oils, paraffin waxes, hard paraffin (paraffinum solidum), Vaseline® and polydecene are preferred.

Suitable paraffin oils are, particularly, liquid paraffin oils (paraffinum liquidum and paraffinum perliquidum). The most preferred hydrocarbon is paraffinum liquidum, also referred to as white oil. Paraffinum liquidum is a mixture of cleaned, saturated, aliphatic hydrocarbons, which mainly includes hydrogen chains with a C-chain distribution from about 25 to about 35 C-atoms.

Preferred fatty constituents are selected from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and/or hydrocarbons. The $C_{12}$-$C_{30}$ fatty alcohols and/or the hydrocarbons are preferred fatty constituents. The $C_{12}$-$C_{30}$ fatty alcohols are particularly preferred fatty constituents.

The component (K2) preferably contains one or multiple fatty constituents in a total amount of from about 5.0 to about 70.0 wt %, preferably from about 10.0 to about 65.0 wt. %, more preferably from about 20.0 to about 60.0 wt % and particularly from about 40.0 to about 60.0 wt. %. In this connection, all amounts are specified in wt. % relative to the total amount of all fatty constituents contained in the component (K2) in relation to the total weight of the component (K2).

With respect to a good and reproducible dilution, it has been found to be particularly preferable that the second component (K2) contains one or multiple hydrocarbons in a total amount of from about 20.0 to about 65.0 wt. %, preferably from about 25.0 to about 60.0 wt. %, more preferably from about 35.0 to about 60.0 wt. %, and particularly from about 40.0 to about 55.0 wt. % relative to the total weight of the second component (K2).

In a particularly preferred embodiment, the method for coloring of human hair is exemplified in that the second component (K2) contains one or multiple hydrocarbons in a total amount of from about 20.0 to about 65.0 wt. %, preferably from about 25.0 to about 60.0 wt. %, more preferably from about 35.0 to about 60.0 wt. % and particularly from about 40.0 to about 55.0 wt. % relative to the total weight of the second component (K2).

The purpose of mixing the dye cream (K1) with the diluent (K2) is a reduction of the pH value and the associated reduction of swelling of the hair during use. Therefore, the mixture (M1) which is produced by mixing (K1) and (K2) has a lower pH value than the dye cream (K1). Consequently, the mixture (M2) which is produced by mixing (M1) with (K3) has a lower pH value than the mixture of (K1) and (K3) (i.e. (M2) has a lower pH value than the undiluted oxidative dye). In this manner, the hairdresser should be able to color the hair of the customer—which may be heavily damaged after repeated color treatments—without changing the color in the accustomed tint, however while avoiding further hair damage, insofar as possible.

The second component (K2) contains at least one acid for reduction of the pH value. A reduction of the pH value without a perceptible color shift (between diluted an undiluted dye) is possible when the component (K2) contains at least one acid from the group including lactic acid, citric acid, maleic acid, tartaric acid, malic acid, succinic acid, oxalic acid, ascorbic acid, sulfuric acid, hydrochloric acid and/or phosphoric acid.

In a particularly preferred embodiment, the method for coloring human hair is exemplified in that the second component (K2) contains at least one acid from the group of lactic acid, citric acid, malic acid, tartaric acid, maleic acid, succinic acid, oxalic acid, ascorbic acid, sulfuric acid, hydrochloric acid and/or phosphoric acid.

In this context, the addition of lactic acid has been found to be particularly preferable.

In a particularly preferred embodiment, the method for coloring human hair is exemplified in that the second component (K2) contains lactic acid.

In order to be able to ensure an effective reduction of the pH value, the acid or acids are preferably added to the component (K2) in a total amount of from about 0.5 to about 15.0 wt. %, more preferably from about 0.5 to about 8.0 wt. %, even more preferably from about 1.5 to about 6.0 wt. % and particularly from about 2.5 to about 5.5 wt. %. In this connection, all amounts are specified in wt. % relative to the total amount of all acids contained in the component (K2) in relation to the total weight of the component (K2).

In a particularly preferred embodiment, the method for coloring of human hair is exemplified in that the second component (K2) contains one or multiple acids in a total amount of from about 0.5 to about 15.0 wt. %, preferably from about 0.5 to about 8.0 wt. %, more preferably from about 1.5 to about 6.0 wt. % and particularly from about 2.5 to about 5.5 wt. % relative to the total weight of the second component (K2).

In a particularly preferred embodiment, the method for coloring human hair is exemplified in that the second component (K2) contains from about 2.5 to about 10.0 wt. % lactic acid relative to the total weight of the second component.

In a preferred embodiment, the method for coloring human hair is exemplified in that the second component (K2) contains from about 3.0 to about 8.0 wt % lactic acid.

In a particularly preferred embodiment, the method for coloring human hair is exemplified in that the second component (K2) contains from about 3.5 to about 6.0 wt. % lactic acid.

In a particularly preferred embodiment, the method for coloring human hair is exemplified in that the second component (K2) contains from about 3.8 to about 5.5 wt. % lactic acid.

In a preferred embodiment, the method for coloring human hair is exemplified in that the second component (K2) contains from about 0.5 to about 15.0 wt. % citric acid.

In a preferred embodiment, the method for coloring human hair is exemplified in that the second component (K2) contains from about 0.5 to about 8.0 wt. % citric acid.

In a particularly preferred embodiment, the method for coloring human hair is exemplified in that the second component (K2) contains from about 1.5 to about 6.0 wt. % citric acid.

In a preferred embodiment, the method for coloring human hair is exemplified in that the second component (K2) contains from about 2.5 to about 5.5 wt. % citric acid.

In a preferred embodiment, the method for coloring human hair is exemplified in that the second component (K2) contains from about 0.5 to about 15.0 wt. % malic acid.

In a preferred embodiment, the method for coloring human hair is exemplified in that the second component (K2) contains from about 0.5 to about 8.0 wt. % malic acid.

In a particularly preferred embodiment, the method for coloring human hair is exemplified in that the second component (K2) contains from about 1.5 to about 6.0 wt. % malic acid.

In a preferred embodiment, the method for coloring human hair is exemplified in that the second component (K2) contains from about 2.5 to about 5.5 wt. % malic acid.

In a preferred embodiment, the method for coloring human hair is exemplified in that the second component (K2) contains from about 0.5 to about 15.0 wt. % tartaric acid.

In a preferred embodiment, the method for coloring human hair is exemplified in that the second component (K2) contains from about 0.5 to about 8.0 wt. % tartaric acid.

In a particularly preferred embodiment, the method for coloring human hair is exemplified in that the second component (K2) contains from about 1.5 to about 6.0 wt. % tartaric acid.

In a preferred embodiment, the method for coloring human hair is exemplified in that the second component (K2) contains from about 2.5 to about 5.5 wt. % tartaric acid.

In a preferred embodiment, the method for coloring human hair is exemplified in that the second component (K2) contains from about 0.5 to about 15.0 wt. % maleic acid.

In a preferred embodiment, the method for coloring human hair is exemplified in that the second component (K2) contains from about 0.5 to about 8.0 wt. % maleic acid.

In a particularly preferred embodiment, the method for coloring human hair is exemplified in that the second component (K2) contains from about 1.5 to about 6.0 wt. % maleic acid.

In a preferred embodiment, the method for coloring human hair is exemplified in that the second component (K2) contains from about 2.5 to about 5.5 wt. % maleic acid.

In a preferred embodiment, the method for coloring human hair is exemplified in that the second component (K2) contains from about 0.5 to about 10.0 wt. % succinic acid.

In a preferred embodiment, the method for coloring human hair is exemplified in that the second component (K2) contains from about 0.5 to about 8.0 wt. % succinic acid.

In a particularly preferred embodiment, the method for coloring human hair is exemplified in that the second component (K2) contains from about 1.5 to about 6.0 wt. % succinic acid.

In a preferred embodiment, the method for coloring human hair is exemplified in that the second component (K2) contains from about 2.5 to about 5.5 wt. % succinic acid.

In a preferred embodiment, the method for coloring human hair is exemplified in that the second component (K2) contains from about 0.5 to about 10.0 wt. % oxalic acid.

In a preferred embodiment, the method for coloring human hair is exemplified in that the second component (K2) contains from about 0.5 to about 8.0 wt. % oxalic acid.

In a particularly preferred embodiment, the method for coloring human hair is exemplified in that the second component (K2) contains from about 1.5 to about 6.0 wt. % oxalic acid.

In a preferred embodiment, the method for coloring human hair is exemplified in that the second component (K2) contains from about 2.5 to about 5.5 wt. % oxalic acid.

In a preferred embodiment, the method for coloring human hair is exemplified in that the second component (K2) contains from about 0.5 to about 15.0 wt. % oxalic acid.

In a preferred embodiment, the method for coloring human hair is exemplified in that the second component (K2) contains from about 0.5 to about 8.0 wt. % ascorbic acid.

In a particularly preferred embodiment, the method for coloring human hair is exemplified in that the second component (K2) contains from about 1.5 to about 6.0 wt. % ascorbic acid.

In a preferred embodiment, the method for coloring human hair is exemplified in that the second component (K2) contains from about 2.5 to about 5.5 wt. % ascorbic acid.

In a preferred embodiment, the method for coloring human hair is exemplified in that the second component (K2) contains from about 0.5 to about 15.0 wt. % phosphoric acid.

In a particularly preferred embodiment, the method for coloring human hair is exemplified in that the second component (K2) contains from about 0.5 to about 8.0 wt. % phosphoric acid.

In a particularly preferred embodiment, the method for coloring human hair is exemplified in that the second component (K2) contains from about 0.5 to about 6.0 wt. % phosphoric acid.

In a preferred embodiment, the method for coloring human hair is exemplified in that the second component (K2) contains from about 2.5 to about 5.5 wt. % phosphoric acid.

In a further preferred embodiment, the component (K2) is aqueous or hydrous. Due to the content of one or multiple acids, the pH value of the component (K2) is acidic and preferably has a value of from about 0.5 to about 5.5, more preferably from about 1.0 to about 4.5, even more preferably from about 1.0 to about 3.0 and particularly from about 1.0 to about 2.5.

In a particularly preferred embodiment, the method for coloring human hair is exemplified in that the second component (K2) is hydrous and has a pH value of from about 0.5 to about 5.5, preferably from about 1.0 to about 4.5, more preferably from about 1.0 to about 3.5 and particularly from about 1.0 to about 2.5.

The pH value can be measured by employing a gas electrode, for example, which is usually in the form of a combination electrode. The pH values according to the present disclosure are pH values that were measured at a temperature of about 22° C.

As described above, the component (K2) is preferably an emulsion containing a proportionately high content of fatty constituents. The water content of the component (K2) is preferably adapted to this content of fatty constituents and within the range of from about 20.0 to about 70.0 wt. %, more preferably from about 24.0 to about 60.0 wt. %, even more preferably from about 24.0 to about 50.0 wt. % and particularly from about 28.0 to about 38.0 wt. %. The specifications in wt. % are also relative to the weight of water in the component (K2) in relation to the total weight of the component (K2).

In a particularly preferred embodiment, the method for coloring of human hair is exemplified in that the second component (K2) has a water content in the range of from about 20.0 to about 70.0 wt. %, preferably from about 24.0 to about 60.0 wt. %, more preferably from about 24.0 to about 50.0 wt. % and particularly from about 28.0 to about 38.0 wt. % relative to the total weight of the second component (K2).

In order to ensure that the component (K2) is present in the form of a stable emulsion, the component (K2) preferably contains one or multiple surfactants. The addition of specific ionic surfactants to the component (K2) can, under certain circumstances, cause a color shift in comparison with an undiluted dye and, therefore, it is preferred that one or multiple nonionic surfactants are added to the component (K2). Nonionic surfactants can also be referred to as nonionic emulsifiers.

In a particularly preferred embodiment, the method for coloring human hair is exemplified in that the second component (K2) contains one or multiple nonionic surfactants.

A nonionic surfactant is a surfactant that does not contain any charges. In other words, a nonionic surfactant does not contain any dissociable functional groups and cannot separate water into ions. Nonionic surfactants are composed of a non-polar part, preferably a hydrocarbon chain (alkyl chain) having at least 8 carbon atoms and a polar part. For example, a polyethylene glycol unit or a (mono- or poly)-saccharide element can be contained in the nonionic surfactant as a polar part.

Fatty alcohols (e.g. $C_8$-$C_{30}$ alkanols) having a fat chain and only one hydroxy group are only very poorly soluble in water and do not have an adequate polar molecular part. In the context of the present disclosure, therefore, fatty alcohols are considered fatty components and explicitly not as nonionic surfactants.

The monoesters and diesters of fatty alcohols (e.g. $C_8$-$C_{30}$ alkanols) and ethylene glycol are also considered fatty substances and explicitly not as nonionic surfactants.

The monoesters, diesters and triesters of fatty alcohols (e.g. $C_8$-$C_{30}$ alkanols) and glycerin are considered fatty substances and explicitly not as nonionic surfactants.

Suitable nonionic surfactants include, for example, at least one polyol group, a polyalkylene glycol ether group or a combination of a polyol and polyglycol ether group. Examples of such compounds include Addition products of from about 5 to about 50 moles of ethylene oxide and/or from about 5 to about 50 moles of propylene oxide on linear and branched fatty alcohols having from 8 to about 30 carbon atoms, such as lauryl-, myristyl-, cetyl-, as well as stearyl-, isostearyl- and oleyl alcohol, on fatty acids having from 8 to about 30 carbon atoms and on alkylphenols having from 8 to about 15 carbon atoms in the alkyl group, with a methyl or $C_2$-$C_6$ alkyl radical end group-closed addition products of from about 5 to about 50 moles of ethylene oxide and/or from about 5 to about 50 moles of propylene oxide on linear and branched fatty alcohols having from 8 to about 30 carbon atoms, on fatty acids having from 8 to about 30 carbon atoms, and on alkyl phenols having from 8 to about 15 carbon atoms in the alkyl group, such as the types available under the trade names Dehydol® LS, Dehydol® LT (Cognis), polyglycerine esters and alkoxylated polyglycerine esters, such as poly(3) glycerin di-isostearate (trade name: Lameform® TGI (Henkel)) and poly(2)glycerin polyhydroxy-stearate (trade name: Dehymuls® PGPH (Henkel)).

Polyol fatty acid esters, such as the commercial product Hydagen® HSP (Cognis) or Sovermol® types (Cognis), high alkoxylated, preferably propoxylated and particularly ethoxylated, mono-, di- and triglycerides, such as glycerin monolaurate+about 20 ethylene oxide and glycerin monostearate+about 20 ethylene oxide, aminoxides, hydroxy mixed ethers, sorbitan fatty acid esters and addition products of ethylene oxide onto sorbitan fatty acid esters such as polysorbates and sorbitan monolaurate+about 20 mole of ethylene oxide (EO), sugar fatty acid esters and addition products of ethylene oxide on sugar fatty acid esters, adducts of ethylene oxide on fatty acid alkanolamides and fatty amines, fatty-acid-n-alkylglucamides, alkyl phenols and alkyl phenol alkoxylates having from 6 to about 21, particularly from 6 to about 15 carbon atoms in the alkyl chain and from 1 to about 30 ethylene oxide and/or propylene oxide units. Preferred representatives of this class are, for example, nonyl phenol+9 EO and octyl phenol+8 EO;

alkyl polyglycosides corresponding to the general formula RO—$(Z)_x$, wherein R denotes alkyl, Z denotes sugar and x denotes the number of sugar units. The alkyl polyglycosides can only contain a certain alkyl radical R. However, these compounds are normally produced from natural fats and oils. In this case, mixtures corresponding to the initial compounds and/or the corresponding reworking of these compounds as alkyl radicals R.

Particularly preferred nonionic surfactants are ethoxylated fatty alcohols and $C_8$-$C_{22}$ alkyl mono- and oligoglycosides.

In a particularly preferred embodiment, the method for coloring human hair is exemplified in that the second component (K2) contains one or multiple ethoxylated fatty alcohols of formula (I),

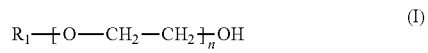

(I)

wherein

R1 denotes a saturated or unsaturated, unbranched or branched $C_8$-$C_{30}$ alkyl group, preferably a saturated, unbranched $C_{16}$ or $C_{18}$ alkyl group, and n denotes an integer from about 10 to about 120, preferably an integer from about 10 to about 80, more preferably an integer from about 10 to about 50 and particularly an integer from about 10 to about 30.

In a particularly preferred embodiment, the method for coloring human hair is exemplified in that the second component (K2) contains one or multiple alkyl mono- or polyglucosides of formula (II),

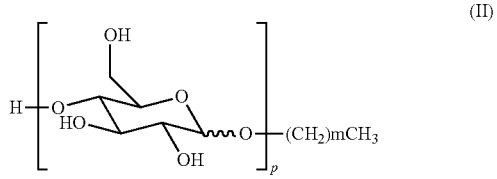

where
m denotes an integer from 7 to about 21, preferably from 9 to about 19, more preferably from 9 to about 17 and particularly from about 11 to about 15 and
p denotes an integer from 1 to 4, preferably from 1 to 3 and particularly from 1 to 2.

The nonionic surfactant or surfactants can be contained in the component (K2) in a total amount of from about 0.5 to about 9.0 wt. %, preferably from about 1.5 to about 7.5 wt. % and particularly from about 3.5 to about 6.5 wt. % relative to the total weight of the component (K2).

As already described above, the addition of ionic or charged surfactants to the color diluent (K2) can cause an undesired color shift in comparison with the undiluted dye, if it is used for the dilution of the oxidative dye arising from (K1) and (K3) (in other words, in comparison with the mixture of (K1) and (K3) alone). The addition of specific silicones and polymers to the component (K2) can also have undesired effects under certain circumstances. For this reason, the component (K2) is preferably packaged so that it essentially comprises fatty components, acids, nonionic surfactants and water. For this reason, it is particularly preferred that the total weight of the fatty components, acid, nonionic surfactants and water amount to at least about 95.0 wt. %, more preferably at least about 97.0 wt. %, even more preferably at least about 99.0 wt. % and particularly about 100.0 wt. % of the total weight of the component (K2).

In a particularly preferred embodiment, the method for dyeing human hair is exemplified in that the second component (K2) contains one or multiple fatty parts and one or multiple acids and one or multiple nonionic surfactants and water, wherein the sum of the amounts of fatty components, acids, nonionic surfactants and water is at least about 95.0 wt. %, preferably at least about 97.0 wt. %, more preferably about 99.0 wt. % and particularly about 100.0 wt. % relative to the total weight of the second component (K2).

The pH value of the mixture (M1), which is produced by mixing (K1) and (K2) should be reduced with the inventive method in comparison to the pH value of the component (K1) in a defined and reproducible manner. Furthermore, the pH value of the mixture (M2), which is produced by mixing (M1) with (K3) should also be reduced in comparison with the mixture (M1) in a defined and reproducible manner. With reduction of the pH value, the damage caused by the (repeated) oxidative coloring is not increased. In this context, it was found that the hair damage can already be significantly reduced when the pH value of the mixture (M1) is at least about 0.2 units lower than the pH value of the component (K1) and when the pH value of the mixture (M2) is at least about 0.2 units lower than the pH value of the mixture (M1).

In a further preferred embodiment, the method for dyeing human hair is exemplified in that
all three components (K1), (K2) and (K3) contain water and
the pH value of the mixture (M1) is at least about 0.2 units lower than the pH value of the component (K1) and
the pH value of the mixture (M2) is at least about 0.2 units lower than the pH value of the mixture (M1).

For reduction of the pH value of the dye cream (K1) and for reduction of its dye content, the color diluent (K2) is mixed with the dye cream (K1). The dye cream (K1) is a component containing at least one oxidation dye precursor of the developer type and at least one oxidation dye precursor of the coupler type.

Preferred additional oxidation dye precursors of the developer type can be selected from the group formed from 2-(1,2-dihydroxyethyl)-p-phenylendiamine, N,N-bis-(2-hydroxyethyl)-p-phenylendiamine, 2-methoxymethyl-p-phenylendiamine, N-(4-amino-3-methylphenyl)-N-[3-(1H-imidazol-1-yl)propyl]amine, N,N'-bis-(2-hydroxyethyl)-N,N-bis-(4-aminophenyl)-1,3-diamino-propane-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-one and the physiologically-tolerated salts thereof.

In a further preferred embodiment, the method for dyeing human hair is exemplified in that
the first component (K1) contains at least one oxidation dye precursor from the group including p-toluylendiamine, 2-(2-hydroxyethyl)-p-phenylendiamine, N,N-bis-(2-hydroxyethyl)-p-phenylendiamine, 2-methoxymethyl-p-phenylendiamine, N-(4-amino-3-methylphenyl)-N-[3-(1H-imidazol-1-yl)propylamine, bis-(2-hydroxy-5-aminophenyl)methane, 4-aminophenol, 4-amino-3-methylphenol, 4,5-diamino-1-(2-hydroxyethyl)pyrazol, 2,4,5,6-tetraaminopyrimidine, 4-hydroxy-2,5,6-triaminopyrimidine, 2-hydroxy-4,5,6-triaminopyrimidine and/or physiologically-tolerated salts thereof.

During the oxidative dyeing process, coupler components do not achieve any significant coloration by themselves. They always require the presence of developer components. As contemplated herein, coupler components permit at least one substitution of a chemical radical of the coupler through the oxidized form of the developer components. At the same time, covalent bonds form between coupler and developer components.

A suitable coupler component as contemplated herein is preferably selected from at least one compound of one of the following classes:
m-aminophenol and/or the derivatives thereof,
m-dihydroxybenzol and/or the derivatives thereof,
m-diaminobenzol and/or the derivatives thereof,
o-diaminobenzol and/or the derivatives thereof,
o-aminophenol derivatives, such as o-aminophenol,
naphthaline derivatives having at least one hydroxy group, di- and/or trihydroxybenzol and/or the derivatives thereof,
pyridine derivatives,
pyrimidine derivatives,
monohydroxyindol derivatives and/or monoaminoindol-derivatives,
monohydroxyindolin derivatives and/or monoaminoindolin derivatives,
pyrazolone derivatives, such as 1-phenyl-3-methylpyrazol-5-on,
morpholine derivatives, such as 6-hydroxybenzomorpholine or 6-aminobenzomorpholine,
quinoxaline derivatives, such as 6-methyl-1,2,3,4-tetrahydroquinoxaline, Mixtures of two or multiple compounds from one or multiple of said classes are likewise preferred according to this embodiment.

Preferred oxidation dye precursors of the coupler type can be selected from the group including 3-aminophenol, 5-amino-2-methylphenol, 3-amino-2-chloro-6-methylphenol, 2-hydroxy-4-aminophenoxy ethanol, 5-amino-4-chloro-2-methylphenol, 5-(2-hydroxyethyl)-amino-2-methylphenol, 2,4-dichloro-3-aminophenol, 2-aminophenol, 3-phenylendiamine, 2-(2,4-diaminophenoxy)ethanol, 1,3-bis(2,4-diaminophenoxy)propane, 1-methoxy-2-amino-4-(2-hydroxyethylamino)benzol (2-amino-4-[(2-hydroxyethyl)amino]-anisole), 1,3-bis(2,4-diaminophenyl)propane, 2,6-bis(2'-hydroxyethylamino)-1-methylbenzol, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzol, resorcin, 2-methylresorcin, 4-chlororesorcin, 1,2,4-trihydroxybenzol, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-on, 1-naphthol, 1,5-dihydroxynaphthaline, 2,7-dihydroxynaphthaline, 1,7-dihydroxynaphthaline, 1,8-dihydroxynaphthaline, 4-hydroxyindole, 6-hydroxyindole, 7-hydroxyindole, 4-hydroxyindoline, 6-hydroxyindoline, 7-hydroxyindoline or mixtures of said compounds or the physiologically compatible salts thereof.

Furthermore, the component (K1) can also contain one or multiple partially-oxidizing dyes.

The pH value of the component (K1) is alkaline. The alkalizing agents for adjustment of the preferred pH values as contemplated herein can be selected from the group formed from ammonia, alkanolamines, basic amino acids, as well as inorganic alkalizing agents, such as (earth) alkali metal hydroxides, (earth) alkali metal metasilicates, (earth) alkali metal phosphates and (earth) alkali metal hydrogen phosphates. Preferred inorganic alkalizing agents are sodium hydroxide, potassium hydroxide, sodium silicate and sodium metasilicate. Organic alkalizing agents usable as contemplated herein are preferably selected from monoethanolamine, 2-amino-2-methylpropanol and triethanolamine. The basic amino acids usable as alkalizing agents as contemplated herein are preferably selected from the group formed from arginine, lysine, ornithine, and histidine, most particularly arginine. However, it emerged during the examinations of the present disclosure that other agents preferred as contemplated herein are exemplified in that they additionally contain an organic alkalizing agent. One embodiment of the first subject matter of the present disclosure is exemplified in that the agent additionally contains at least one alkalizing agent, which is selected from the group formed from ammonia, alkanolamines and basic amino acids, more particularly from ammonia, monoethanolamine and arginine or the tolerated salts thereof.

The pH value can be measured by employing a gas electrode, for example, which is usually in the form of a combination electrode. The pH values according to the present disclosure are pH values that were measured at a temperature of about 22° C. In a further embodiment, particular preference is given to a method for coloring of human hair, including the following steps in the specified sequence A) Mixing a first component (K1) with a second component (K2) to produce a first mixture (M1),
B) Mixing the mixture (M1) with a third component (K3) to produce a second mixture (M2),
C) Application of the mixture (M2) on the hair,
D) Allowing the mixture (M2) to take effect for a period of from about 30 seconds to about 45 minutes,
E) Rinsing the mixture (M2) from the hair,
wherein
the first component (K1) is a dye preparation containing at least one oxidation dye precursor of the developer type and at least one oxidation dye precursor of the coupler type and ammonia in a cosmetic carrier,
the second component (K2) is a "color diluent" which does not contain any oxidation dye precursors or oxidants and
the third component (K3) is an oxidant preparation containing hydrogen peroxide in a cosmetic carrier.

The mixture (M1) produced by mixing (K1) and (K2) is mixed with the component (K3) in process step B) as contemplated herein. The component (K3) is an oxidant preparation containing at least one oxidant. It is particularly preferred that the oxidant is hydrogen peroxide.

The person skilled in the art will choose the amount of oxidant depending on the desired lightening effect. If the development of a very dark shade is desired, the person skilled in the art will reduce the amount of hydrogen peroxide accordingly. However, if a lightening fashionable tint on dark hair should be achieved, the hair must also be lightened to a significant extent at the same time. In this case, the chosen amount of hydrogen peroxide used is appropriately high. The oxidant preparation (K3) can contain from about 1.5 to about 12.5 wt. %, preferably from about 2.5 to about 10.5 wt. %, more preferably from about 3.0 to about 9.0 wt. % hydrogen peroxide (calculated as 100% hydrogen peroxide) relative to the total weight of the component (K3).

In a further preferred embodiment, the method for dyeing human hair is exemplified in that the third component (K3) contains from about 1.5 to about 12.5 wt. %, preferably from about 2.5 to about 10.5 wt. %, more preferably from about 3.0 to about 9.0 wt. % hydrogen peroxide relative to the total weight of the component (K3).

Moreover, the component (K1) and/or the component (K3) can also contain additional active ingredients, adjuvants and additives, such as fatty components, surfactants, nonionic polymers such as vinylpyrrolidinone/vinylacrylate-copolymers, polyvinylpyrrolidinone, vinylpyrrolidinone/vinylacetate-copolymers, polyethyleneglycols and polysiloxanes; additional silicones such as volatile or non-volatile, straight-chained, branched or cyclical, cross-linked or non-cross-linked polyalkylsiloxanes (such as dimethicones or cyclomethicones), polyarylsiloxanes and/or polyalkylarylsiloxanes, more particularly polysiloxanes with organofunctional groups such as substituted or unsubstituted amines (amodimethicones), carboxyl-, alkoxy- and/or hydroxyl groups (dimethiconecopolyols), linear polysiloxan (A)-polyoxyalkylen(B)-block copolymers, grafted silicon polymers; cationic polymers such as quaternized cellulose ether, polysiloxanes with quaternary groups, dimethyldiallylammoniumchloride-polymers, acrylamide-dimethyldiallyl-ammonium chloride copolymers, with diethylsulfate quaternated dimethylamino-ethylmethacrylate-vinylpyrrolidinone-copolymers, vinylpyrrolidinone-imidazoliniummethochloride-copolymers and quaternated polyvinylalcohol; zwitterionic and amphoteric polymers; anionic polymers such as polyacryl acids or cross-linked polyacryl acids; structurants, such as glucose, malic acid and lactic acid, hair-conditioning compounds such as phospholipides, for example lecithin and kephaline; perfume oils, dimethylisosorbide and cyclodextrine; fiber structure-improving agents, more particularly mono-, di- and oligosaccharides, such as glucose, galactose, fructose, fruit sugar and lactose; dyes for coloring the preparations; anti-dandruff active ingredients such as piroctone olamine, zinc omadine and climbazole; amino acids and oligopeptides; protein hydrolysates on an animal and/or plant basis, as well as in the form of their fatty acid condensation products or, where applicable, anionically or cationically modified derivatives; plant oils; light stabilizers and UV blockers; active ingredients such as panthenol, pantothenic acid, pantolacton, allantoin, pyrrolidinonecarbonic acids and the salts thereof, as well as bisabolol; polyphenols, more particularly hydroxy cinnamic acids, 6,7-dihydroxycumarines, hydroxybenzoic acids, catechins, tannins, leukoanthocyanidine, anthocyanidine, flavanons, flavons and flavonols; ceramides or pseudoceramides; vitamins, provitamins and vitamin precursors; plant extracts; fats and waxes such as fatty alcohols, beeswax, montan wax and paraffins; source and penetration substances such as glycerin, propylene glycolmonoethylether, carbonate, hydrogen carbonate, guanidine, urea, as well as primary, secondary and tertiary phosphates; opacifiers such as latex, styrene/PVP and styrene/acrylamide copolymers; pearl shine concentrates such as ethyleneglycolmono- and -distearate as well as PEG-3-distearate; pigments as well as propellants such as propane-butane-mixtures, $N_2O$, dimethylether, $CO_2$ and air.

The components (K1) and (K2) are preferably mixed together in specific quantity ranges in the method as contemplated herein. The first component (K1) and the second component (K2) can be mixed together, for example, in a quantity ratio of from about 3:1 to about 1:3, preferably from about 2:1 to about 2:1.

The components (K1) and (K2) are preferably mixed together in specific quantity ranges in the method as contemplated herein. The first mixture (M1) and the third mixture (M2) can be mixed together, for example, in a quantity ratio of from about 3:1 to about 1:3, preferably from about 2:1 to about 1:2.

EXAMPLE

If 200 g of the component (K1) are mixed with 100 g of the component (K2) in step A), the quantity ratio is 2:1.

In a further preferred embodiment, the method for dyeing human hair is exemplified in that
A) the first component (K1) and the second component (K2) can be mixed together, for example, in a quantity ratio of from about 3:1 to about 1:3, preferably from about 2:1 to about 1:2 and B) the mixture (M1) and the third component (K3) can be mixed together, for example, in a quantity ratio of from about 3:1 to about 1:3, preferably from about 2:1 to about 1:2.

As already described above, the method as contemplated herein should give the hairdresser the ability to treat damaged regions of the hair with a less-damaging oxidative dye.

In damaged hair, the cuticula, the cuticle of the hair, is damaged to a greater or lesser degree. As a result, there is generally greater color uptake on damaged hair. Therefore, if the hairline and tips are dyed with the same coloring agent, there is always the risk of an uneven coloring result with heavily damaged hair.

The present disclosure also addresses the second problem of providing the hairdresser a system with which they can simply, purposefully and exactly reproducibly reduce the dye concentration in the hair coloring agent after assessing the degree of damage of the hair to be dyed.

Depending on the degree of damage of the respective hair region, the hairdresser can preferably choose whether they apply the mixture (M2) in step C) of the method or they apply the mixture (M2) to only specific hair regions.

In a further preferred embodiment, the method for dyeing human hair is exemplified in that
C) the mixture (M2) is applied to the hairline or in the region of the hair length/tips.

Furthermore, the hairdresser can also choose to vary the exposure time of the mixture (M2) on specific hair regions depending on the degree of damage.

After application on the hair, the mixture (M2) is left on the hair to take effect for a period of from about 30 seconds to about 45 minutes in step D). In the process, it is possible and inventive to leave the mixture (M2) on all regions of the hair for a specific time period. In a further embodiment, however, it is also possible to choose different exposure periods for specific regions of the hair so that the exposure period in the region of the hairline, for instance, is longer than the exposure period in the region of the damaged tips.

In a further preferred embodiment, the method for dyeing human hair is exemplified in that
D1) the mixture (M2) is applied on the hair in the region of the hairline or the hair length/tips for a period of from about 30 seconds to about 45 minutes and
D2) the mixture (M2) is applied on the hair in the region which was not treated in step D1) for a period of from about 30 seconds to about 45 minutes,
wherein the application durations of steps D1) and D2) differ by at least about 5 minutes, preferably at least about 10 minutes.

If, for example, the hair is heavily damaged in the overall region—also directly at the hairline—, the hairdresser can
D1) apply the mixture (M2) on the hair in the region of the hairline for a period of from about 35 to about 45 minutes and
D2) apply the mixture (M2) on the hair in the region apart from the hairline for a period of only from about 25 to about 30 minutes.

If only the tips are heavily damaged, the hairdresser can
D1) apply the mixture (M2) on the hair tips for a period of from about 15 to about 25 minutes and
D2) apply the mixture (M2) on the hair in the region apart from the hair tips for a period of only from about 25 to about 30 minutes.

In the context of the present disclosure, the hairline is understood to mean the region of the hair directly on the scalp (the first 0 to about 5 cm of the hair).

The hair length or hair tips are understood to mean the last from about 5 to about 10 cm of the hair depending on the length of the hair.

EXAMPLES

The following formulations have been produced—unless otherwise stated, all values refer to percentage by weight.

Dye preparation (first component (K1))

|  | wt. % |
|---|---|
| Polyacrylic acid (ammonium salt) 0.5% hydrous solution | 15.0 |
| Decyloleate | 2.1 |
| Sodium cetearyl sulfate | 1.3 |
| Cetearyl alcohol | 14.9 |
| Glyceryl stearate | 5.4 |
| Linoleamidopropyl PG-dimoniumchloride phosphate | 0.05 |
| EDTA | 0.8 |
| Monoethanolamine | 0.4 |
| Ammonia (25% hydrous solution) | 8.0 |
| Ascorbic acid | 0.1 |
| Sodium dithionite | 0.1 |
| L-Serin0 | 0.3 |
| Polyquaternium-2 | 0.1 |
| p-toluylendiamine, sulfate | 0.8 |
| Resorcin | 0.2 |
| m-aminophenol | 0.04 |
| 4-chlororesorcin | 0.2 |
| 2-amino-4-[(2-hydroxyethyl)amino]-anisole | 0.02 |
| Water | ad 100 |

Color diluent (component (K2))

|  | wt. % |
|---|---|
| Lactic acid | 4.0 |
| Paraffinium Liquidum | 50.0 |
| Cetearyl alcohol | 3.4 |
| Ceteareth-20 | 5.5 |
| Glyceryl stearate | 3.4 |
| Water | Ad 100 (pH = 1.79) |

Oxidant preparation (Component (K3))

|  | wt. % |
|---|---|
| Sodium benzoate | 0.04 |
| Dipicolinic acid | 0.1 |
| Di-sodium pyrophosphate | 0.1 |
| Potassium hydroxide | 0.1 |
| 1,2-Propanediol | 1.0 |
| Etidronic acid (1-hydroxyethane-1,1-diphosphonic acid) | 0.2 |
| Paraffinum liquidum | 0.3 |
| Steartrimonium chloride | 0.4 |
| Cetearyl alcohol | 3.4 |
| Ceteareth-20 | 1.0 |
| Hydrogen peroxide | 6.1 |
| Water | ad 100 |

Application

First the dye preparation (K1) was mixed with the color diluent (K2). The mixture (M1) was obtained in this mixing process.

Then the mixture (M1) was mixed with the oxidant preparation (K3). The mixture (M2) was produced for this purpose.

The following pH values were obtained

|  | (K1) + (K3) Comparison | [(K1) + (K2)] + (K3) Present disclosure |
|---|---|---|
| pH value | 10.05 | 9.78 |

The invention claimed is:

1. A method for dyeing human hair, comprising the following steps in the specified sequence:
   A) mixing a first component (K1) with a second component (K2) to produce a first mixture (M1), wherein the first component (K1) is a dye preparation comprising at least one oxidation dye precursor, and wherein the second component (K2) is a color diluent which does not contain any oxidation dye precursors or oxidants, and wherein the second component (K2) is hydrous and has a pH value of from about 0.5 to about 5.5;
   B) mixing the first mixture (M1) with a third component (K3) to produce a second mixture (M2), wherein the third component (K3) is an oxidant preparation comprising at least one oxidant;
   C) applying the second mixture (M2) on the hair;
   D) allowing the second mixture (M2) to take effect for a period of from about 30 seconds to about 45 minutes; and
   E) rinsing the second mixture (M2) from the hair.

2. The method according to claim 1, wherein the second component (K2) comprises one or multiple fatty constituents in a total amount of from about 5.0 to about 70.0 wt %, relative to a total weight of the second component (K2).

3. The method according to claim 1, wherein the second component (K2) comprises one or multiple hydrocarbons in a total amount of from about 20.0 to about 65.0 wt. %, relative to a total weight of the second component (K2).

4. The method according to claim 1, wherein the second component (K2) comprises at least one acid from the group of lactic acid, citric acid, malic acid, tartaric acid, maleic acid, succinic acid, oxalic acid, ascorbic acid, sulfuric acid, hydrochloric acid and/or phosphoric acid.

5. The method according to claim 1, wherein the second component (K2) comprises one or multiple acids in a total amount of from about 0.5 to about 15.0 wt %, relative to a total weight of the second component (K2).

6. The method according to claim 1, wherein the second component (K2) comprises a water content of from about 20.0 to about 70.0 wt. %, relative to a total weight of the second component (K2).

7. The method according to claim 1, wherein the second component (K2) comprises one or multiple nonionic surfactants.

8. The method according to claim 1, wherein the second component (K2) comprises one or multiple fatty constituents and one or multiple acids and one or multiple nonionic surfactants and water, wherein the sum of the amounts of the one or multiple fatty constituents, the one or multiple acids, the one or multiple nonionic surfactants and water is at least about 95.0 wt. %, relative to a total weight of the second component (K2).

9. A method for dyeing human hair, comprising the following steps in the specified sequence:
   A) mixing a first component (K1) with a second component (K2) to produce a first mixture (M1), wherein the first component (K1) is a dye preparation comprising at least one oxidation dye precursor, and wherein the second component (K2) is a color diluent which does not contain any oxidation dye precursors or oxidants;

B) mixing the first mixture (M1) with a third component (K3) to produce a second mixture (M2), wherein the third component (K3) is an oxidant preparation comprising at least one oxidant;

C) applying the second mixture (M2) on the hair;

D) allowing the second mixture (M2) to take effect for a period of from about 30 seconds to about 45 minutes; and E) rinsing the second mixture (M2) from the hair, wherein:
all three components (K1), (K2) and (K3) comprise water and
the pH value of the first mixture (M1) is at least about 0.2 units lower than the pH value of the component (K1) and
the pH value of the second mixture (M2) is at least about 0.2 units lower than the pH value of the first mixture (M1).

10. The method according to claim 1, wherein
the first component (K1) comprises at least one oxidation dye precursor from the group of p-toluylendiamine, 2-(2-hydroxyethyl)-p-phenylendiamine, N,N-bis-(2-hydroxyethyl)-p-phenylendiamine, 2-methoxymethyl-p-phenylendiamine, N-(4-amino-3-methylphenyl)-N-[3-(1H-imidazol-1-yl)propylamine, bis-(2-hydroxy-5-aminophenyl)methane, 4-aminophenol, 4-amino-3-methylphenol, 4,5-diamino-1-(2-hydroxyethyl) pyrazol, 2,4,5,6-tetraaminopyrimidine, 4-hydroxy-2,5,6-triaminopyrimidine, 2-hydroxy-4,5,6-triaminopyrimidine and/or physiologically-tolerated salts thereof.

11. The method according to claim 1, wherein
the third component (K3) comprises from about 1.5 to about 12.5 wt. %, hydrogen peroxide relative to a total weight of the component (K3).

12. The method according to claim 1, wherein
A) the first component (K1) and the second component (K2) are mixed together in a quantity ratio of from about 3:1 to about 1:3; and
B) the first mixture (M1) and the third component (K3) are mixed together in a quantity ratio of from about 3:1 to about 1:3.

13. The method according to claim 1, wherein
C) the second mixture (M2) is applied to a hairline.

14. The method according to claim 1, wherein
D1) the second mixture (M2) is applied on the hair in a region of the hairline for a period of from about 30 seconds to about 45 minutes and D2) the second mixture (M2) is applied on the hair in the region which was not treated in step D1) for a period of from about 30 seconds to about 45 minutes,
wherein the application durations of steps D1) and D2) differ by at least about 5 minutes, and wherein steps D1 and D2 comprise two separate application steps performed at different times.

15. The method according to claim 1 wherein:
C) the second mixture (M2) is applied to a region of the hair length/tips, wherein the region of the hair length/tips comprises the last about 5 to about 10 centimeters of the hair.

16. A method for dyeing human hair, comprising the following steps in the specified sequence:

A) mixing a first component (K1) with a second component (K2) to produce a first mixture (M1), wherein the first component (K1) is a dye preparation comprising at least one oxidation dye precursor, and wherein the second component (K2) is a color diluent which does not contain any oxidation dye precursors or oxidants and comprises one or multiple fatty constituents in a total amount of from about 40.0 to about 60.0 wt %, relative to a total weight of the second component (K2);

B) mixing the first mixture (M1) with a third component (K3) to produce a second mixture (M2), wherein the third component (K3) is an oxidant preparation comprising at least one oxidant;

C) applying the second mixture (M2) on the hair;

D) allowing the second mixture (M2) to take effect for a period of from about 30 seconds to about 45 minutes; and E) rinsing the second mixture (M2) from the hair.

17. The method according to claim 16 wherein:
the second component (K2) comprises one or multiple hydrocarbons in a total amount of from about 40.0 to about 55.0 wt. %, relative to a total weight of the second component (K2).

18. The method according to claim 17 wherein:
the second component (K2) comprises one or multiple acids in a total amount of from about 2.5 to about 5.5 wt %, relative to a total weight of the second component (K2).

19. The method according to claim 18 wherein:
the second component (K2) is hydrous and has a pH value of from about 1.0 to about 2.5.

20. The method according to claim 16 wherein:
C) the second mixture (M2) is applied to a region of the hair length/tips, wherein the region of the hair length/tips comprises the last about 5 to about 10 centimeters of the hair.

* * * * *